United States Patent [19]

Dougherty

[11] Patent Number: 5,286,890
[45] Date of Patent: Feb. 15, 1994

[54] AROMATIC AMINE TERMINATED SILICONE MONOMERS, OLIGOMERS, AND POLYMERS THEREFROM

[75] Inventor: Thomas K. Dougherty, Playa Del Rey, Calif.

[73] Assignee: Hughes Aircraft Company, Los Angeles, Calif.

[21] Appl. No.: 870,432

[22] Filed: Apr. 16, 1992

[51] Int. Cl.$^5$ .............................. C07F 7/04; C07F 7/10
[52] U.S. Cl. .................................. 556/425; 556/413; 528/33; 528/36; 528/38
[58] Field of Search ................... 556/413, 425; 528/33, 528/36, 38

[56] References Cited

U.S. PATENT DOCUMENTS

| | | | |
|---|---|---|---|
| 4,981,988 | 1/1991 | Ichinohe et al. | 556/425 |
| 5,021,532 | 6/1991 | Sugita et al. | 556/425 X |
| 5,021,585 | 6/1991 | Dougherty et al. | 548/406 |
| 5,075,475 | 12/1991 | Dougherty et al. | 556/412 |
| 5,081,201 | 1/1992 | Dougherty et al. | 528/33 |

FOREIGN PATENT DOCUMENTS 63-169561 7/1988 Japan .

OTHER PUBLICATIONS

J. C. Bonnet et al, *Bulletin de la Societe Chimique de France*, vol. 1972, pp. 3561-3579 (1972).

R. de Surville et al, *Electrochimica Acta*, vol. 13, p. 1451 et seq. (1968).

T. L. Guggenheim, "Protection of Substituted Anilines with 1,1,4,4-tetramethyl-1,4-bis(N,N-dimethylamino)-disilethylene", *Tetrahedron Letters*, vol. 25, No. 12, pp. 1253-1254 (1984).

V. H. Kuckertz, *Die Makromolekulare Chemie*, vol. 98, pp. 101-108 (1966).

P. P. Policastro et al, "Siloxane Polyimides for Interlevel Dielectric Applications", in the *Proceedings of the ACS Division of Polymeric Materials: Science and Engineering*, vol. 59, pp. 209-213 (Los Angeles, Calif., 1988).

*Primary Examiner*—Arthur C. Prescott
*Attorney, Agent, or Firm*—M. E. Lachman; M. W. Sales; W. K. Denson-Low

[57] ABSTRACT

Novel aniline terminated silicone monomers with (a) silane (Si—H) functionalities, (b) silanol (Si—OH) functionalities, or (c) alpha,omega-aniline terminated polydimethyl siloxanes, and a novel synthetic route. The alpha,omega-aniline terminated dimethyl siloxanes are prepared, starting with bromoaniline, in which the amine functionality is protected, such as by reaction with 1,1,4,4-tetramethyl-1,4-bis(N,N-diethylamino)-1,4-disilabutane, to form 1-(bromophenyl)-2,2,5,5-tetramethyl-l-aza-2,5-disilacyclopentane. The protected bromoaniline is then reacted with n-butyllithium and chlorodialkylsilane to form 1-((dialkylsilyl)phenyl)-2,2,5,5-tetramethyl-l-aza-2,5-disilacyclopentane. Next, the protected dimethylsilane aniline is subjected to deprotection to form aminophenyldialkyl silane, which is considered to be novel. This silane is then hydrolyzed to form the corresponding silanol, also considered to be novel. The silanol is then condensed to form bis(aminophenyl)-1,1,3,3-tetraalkyldisiloxane. The amino group is in either the meta or para position, depending on the position of the bromo functionality in bromoaniline. The disiloxanes may be reacted further to form oligomers and polymers and may also be used to form copolymers.

32 Claims, No Drawings

AROMATIC AMINE TERMINATED SILICONE MONOMERS, OLIGOMERS, AND POLYMERS THEREFROM

BACKGROUND OF THE INVENTION

1. Field of the Invention

The present invention relates generally to silicon-containing compounds, methods for the preparation of such compounds, and polymers thereof. More particularly, the present invention relates to aromatic amine terminated silicone monomers, oligomers, and polymers thereof.

2. Description of Related Art

Polyimides are widely used in the electronics and aerospace industry, f or example, as coatings, adhesives, and interlevel insulators in integrated circuits, and also to form composites and other structures.

Silicon-containing imides, specifically, silanol- and silyl-terminated aromatic imide oligomers, have been disclosed and claimed in a series of patents assigned to the same assignee as the present application: U.S. Pat. Nos. 5,021,585; 5,075,475; and 5,081,201. These compounds possess good optical properties, good thermo-oxidative stability, resistance to atomic oxygen degradation, good mechanical properties, and good processing characteristics.

Japanese Published Unexamined Patent Application 63-169561 discloses silicone-imide copolymers for flexible printed circuit boards, insulating material for heavy electric machines, carrier tapes, thermal resistant coating material for electric wire, and the like. This patent discloses the preparation of bis(3-aminophenyl)-1,1,3,3-tetramethylsiloxane as an intermediate in the reaction sequence to preparing the polymers of the invention. However, the synthetic route to forming the siloxane follows classical methods and requires several reaction steps.

The monomer bisaminophenyltetramethyl disiloxane is described in two articles, V. H. Kuckertz, *Die Makromolekulare Chemie*, Vol. 98, pp. 101–108 (1966) and J. C. Bonnet et al, *Bulletin de la Societe Chimique de France*, Vol. 1972, pp. 3561–3579 (1972).

The first reference describes polyimides prepared from the above monomer which are brittle and less soluble as compared to the aliphatic counterpart. The synthesis of the diamine in both references is through classical nitration chemistry, which most likely gives impure and isomeric monomers.

The second reference describes the diamino monomer, but does not describe polyimides.

Other aromatic polyimide siloxanes are described in another reference, P. P. Policastro et al, "Siloxane Polyimides for Interlevel Dielectric Applications", in the *Proceedings of the ACS Division of Polymeric Materials: Science and Engineering*, Vol. 59, pp. 209–213 (Los Angeles, Calif., 1988). These materials are made from a silicone anhydride.

There remains a need to continue to develop new materials which have novel electrical, electronic, and optical properties for use in the dissipation of spacecraft charging or electronic applications, for example.

SUMMARY OF THE INVENTION

In accordance with the invention, novel aniline terminated silicone monomers with (a) silane (Si—H) functionalities, (b) silanol (Si—OH) functionalities, or (c) alpha, omega-aniline terminated polydimethyl siloxanes are disclosed, together with novel preparative procedures.

The alpha,omega-aniline terminated dimethyl siloxanes are prepared, starting with 3-bromoaniline, in which the amine functionality is protected, such as by reaction with 1,1,4,4-tetramethyl-1,4-bis(N,N-diethylamino)-1,4-disilabutane, to form 1-(3-bromophenyl)-2,2,5,5-tetramethyl-1-aza-2,5-disilacyclopentane. The protected bromoaniline is then reacted with an alkyllithium or with magnesium to form the corresponding lithio or Grignard compound, respectively, which is then reacted with chlorodialkylsilane to form 1-(3-(dialkylsilyl)phenyl)-2,2,5,5-tetramethyl-1-aza-2,5-disilacyclopentane. This reaction places the silane functionality in the meta position. Next, the protected dimethylsilane aniline is subjected to deprotection to form 3-aminophenyldialkyl silane, which is considered to be novel. This silane is then hydrolyzed to form the corresponding silanol, also considered to be novel. The silanol is then condensed to form bis(3-aminophenyl)-1,1,3,3-tetraalkyldisiloxane.

The corresponding novel para compound, bis(4-aminophenyl)-1,1,3,3-tetraalkylsiloxane, is made starting with 4-bromoaniline and following the same synthetic route as described above.

The disiloxanes may be reacted further to form oligomers and polymers and may also be used to form copolymers.

In contrast to the classical nitration synthesis of the prior art, the synthetic route of the present invention is modern and gives single isomers of high purity.

DESCRIPTION OF THE PREFERRED EMBODIMENTS

The aromatic amine terminated silicone monomers of the present invention are represented by Formula 1, below, which indicates attachment of the amine radical in either the ortho, meta, or para position. The meta and para isomers are preferred. While the meta compound is known, the para compound is novel.

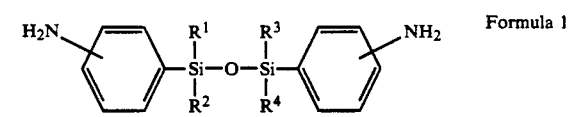

Formula 1 where $R^1$, $R^2$, $R^3$, and $R^4$ are each selected from the group consisting of $C_1$ to $C_6$ alkyl, phenyl, or phenyl substituted with one or more alkyl or halogen groups.

The synthesis of the compound of Formula 1 is achieved in accordance with the present invention by protecting the amine functionality on bromoaniline. Such protection is done, for example, following the teachings of T. L. Guggenheim in "Protection of Substituted Anilines with 1,1,4,4-tetramethyl-1,4-bis(N,N-dimethylamino)disilethylene", *Tetrahedron Letters*, Vol. 25, No. 12, pp.1253–1254 (1984) to provide the protected aniline as follows:

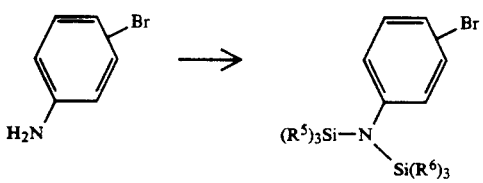

In the protected aniline, $R^5$ and $R^6$ are each a $C_1$ to $C_4$ alkyl group. Alternatively, and preferably, the group $-NSi(R^5)_3Si(R^6)_3$ is 2,2,5,5-tetramethyl-1-aza-2,5-disilacyclopentane. In this latter case, the protected aniline is formed by reacting bromoaniline with 1,1,4,4-tetramethyl-1,4-bis (N,N-diethylamino) -1, 4-disilabutane to form 1-bromophenyl-2,2,5,5-tetramethyl-1-aza-2,5-disilacyclopentane:

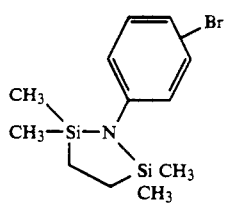

The protected bromoaniline is then reacted with an alkyllithium compound, such as n-butyllithium, or with magnesium to form the corresponding lithio or Grignard compound, respectively, followed by reaction with a halogenated compound, such as chlorodialkylsilane, to form the following silane, shown here as the general formula:

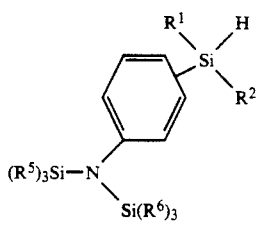

As taught in U.S. Pat. No. 5,075,475, this reaction replaces the bromine with the silane functionality. Next, the protected dialkylsilane aniline is subjected to deprotection to form the corresponding dialkylsilane aniline, which is considered to be novel. The silane is deprotected by hydrolysis reaction in the presence of acid or base. This silane is then hydrolyzed to form the corresponding silanol, also considered to be novel.

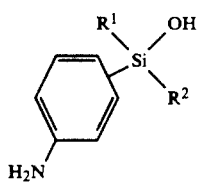

The silanol is then condensed by known methods, described, for example, in U.S. Pat. No. 5,075,475, to form bis-aminophenyl)-1,1,3,3-tetraalkyldisiloxane. The para compound, bis (4-aminophenyl)-1,1,3,3-tetraalkyldisiloxane, is considered to be novel, as discussed below.

The reaction scheme I below depicts the reaction sequence to form the desired meta monomer. The synthesis of the meta compound of Formula 1 is achieved in accordance with the present invention by protecting the amine functionality on 3-bromoaniline. Such protection is done, for example, following the teachings of T. L. Guggenheim, supra, in which, as described above, the group $-NSi(R^5)_3Si(R^6)_3$ is preferably 2,2,5,5-tetramethyl-1-aza-2,5-disilacyclopentane, to thereby form 1-(3-bromophenyl)-2,2,5,5-tetramethyl-1-aza-2,5-disilacyclopentane (IA). The protected bromoaniline is then reacted with an alkyllithium compound, such as n-butyllithium, or with magnesium to form the corresponding lithio or Grignard compound, respectively, followed by reaction with a halogenated compound, such as chlorodialkylsilane, to form 1-(3-(dialkylsilyl)-phenyl)-2,2,5,5-tetramethyl-1-aza-2,5-disilacyclopentane (IB). As taught in U.S. Pat. No. 5,075,475, this reaction places the silane functionality in the meta position, replacing the bromine. Next, the protected dimethylsilane aniline is subjected to deprotection to form 3-aminophenyldialkyl silane (IC), which is considered to be novel. The silane is deprotected by hydrolysis reaction in the presence of acid or base. This silane is then hydrolyzed to form the corresponding silanol (ID), also considered to be novel. The silanol is then condensed by known methods, described, for example, in U.S. Pat. No. 5,075,475, to form bis(3-aminophenyl)-1,1,3,3-tetraalkyldisiloxane (IE).

Reaction Scheme I

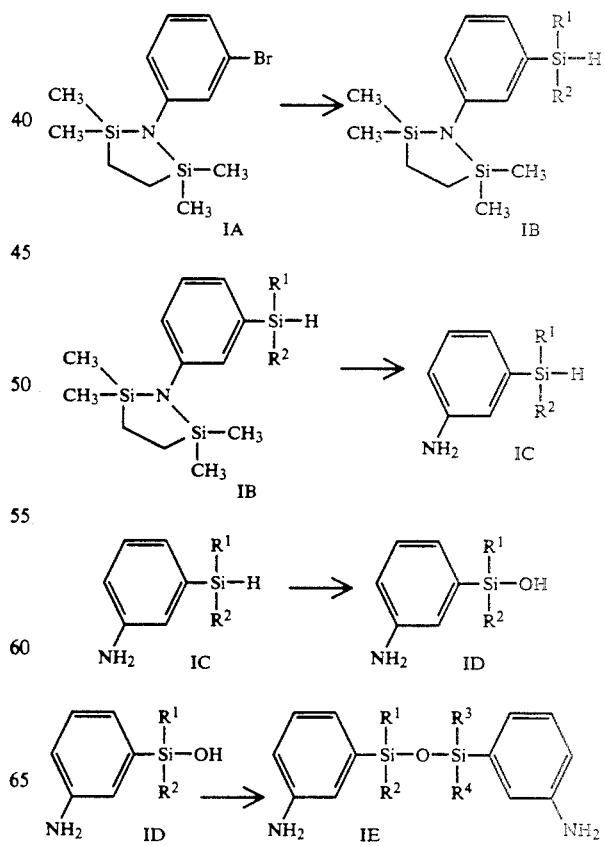

The corresponding novel para compound, bis(4-aminophenyl)-1,1,3,3-tetraalkylsiloxane, is made starting with 4-bromoaniline and following the same synthetic route as described above. The reaction scheme II below depicts the reaction sequence to form the desired para monomer. The synthesis of the para compound of Formula 1 is achieved in accordance with the present invention by protecting the amine functionality on 4-bromoaniline. Such protection is done, for example, following the teachings of Guggenheim, previously referenced. Preferably, reaction is done with 1,1,4,4-tetramethyl-1,4-bis(N,N-diethylamino)-1,4-disilabutane, to form 1-(4-bromophenyl)-2,2,5,5-tetramethyl-1-aza-2,5-disilacyclopentane (IIA). The protected bromoaniline is then reacted with an alkyllithium compound, such as n-butyllithium, or with magnesium, and then with a halogenated compound, such as chlorodialkylsilane, to form 1-(4-(dialkylsilyl)phenyl)-2,2,5,5-tetramethyl-1-aza-2,5-disilacyclopentane (IIB). As taught in U.S. Pat. No. 5,075,475, this reaction places the silane functionality in the para position, replacing the bromine. Next, the protected dimethylsilane aniline is subjected to deprotection to form 4-aminophenyldialkyl silane (IIC), which is considered to be novel. The silane is deprotected by hydrolysis reaction in the presence of acid or base. This silane is then hydrolyzed to form the corresponding silanol (IID), also considered to be novel. The silanol is then condensed to form bis(4-aminophenyl)-1,1,-3,3-tetraalkyldisiloxane (IIE), also considered to be novel. n Reaction Scheme II

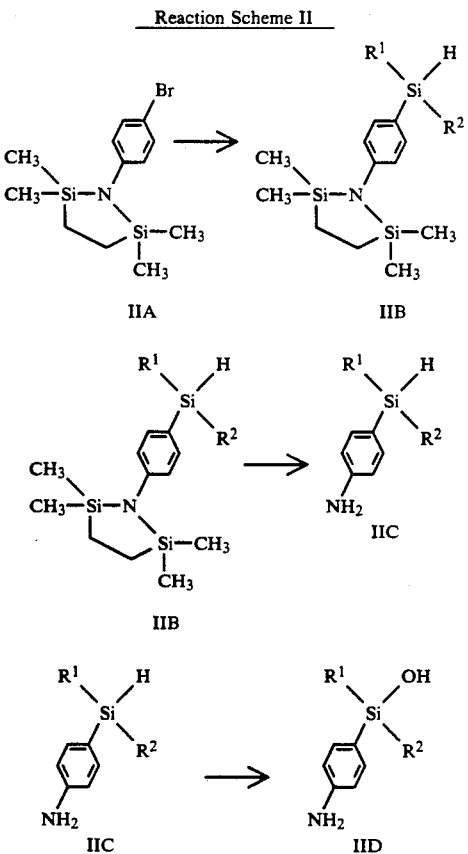

-continued
Reaction Scheme II

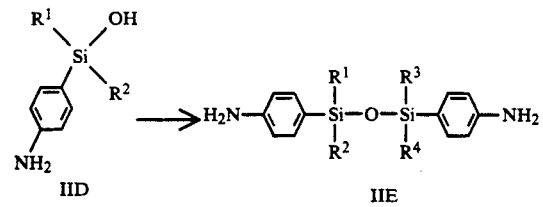

Compounds IE or IIE can be reacted with a cyclic siloxane, having ≧3 silicon atoms, each substituted with $R^1$ and $R^2$, such as octamethyl tetracyclosiloxane, to form oligomers and polymers having Formula 2:

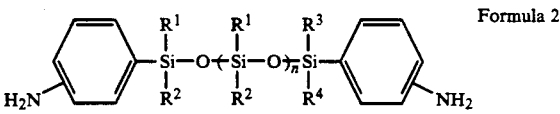

Formula 2

The value of n is not critical. However, it will be appreciated that the larger the value of n, the more the compound acts like a silicone and less like an amine. Preferably, n ranges from 1 to 20. In practice, a mixture of these compounds with different values of n is formed.

The present invention comprises the chemical synthesis of aromatic amine terminated siloxane monomers and oligomers useful for the production of a variety of different polymer materials. The materials formed consist of three major classes of novel polymers:

1. New conductive polymers based on functionalized polyaniline systems;
2. Aromatic silicone-modified polyimides; and
3. Polymers made in accordance with the teachings of the present invention as a curing agent for epoxy resins, isocyanate resins, and others.

Each of these classes is discussed separately below.

1. Silicone-Based Polyanilines.

The present invention contemplates aniline terminated silicone monomers with a silane (Si—H) functionality (IC and IIC above), silanol (Si—OH) functionality (ID and IID above), or alpha,omega-aniline terminated dimethyl siloxanes (IE and IIE above). By incorporating these monomers into various polymers and then further polymerizing the functionality by a polyaniline-type polymerization as described, for example, by R. deSurville et al, Electrochimica Acta, Vol. 13, p. 1451 et seq. (1968), new materials with improved properties which are electrically conductive, have novel electro-optical properties, and/or may be useful for the incorporation into improved gas separation membranes can be constructed.

The silane-modified aniline compounds (IB, IIB, and-/or IC, IIC) can be used to chemically graft (covalent attachment) the aniline (or protected aniline) function onto vinyl-containing molecules or polymers to give aniline-attached functions to these molecules/polymers. Subsequent oxidative aniline polymerization will give chemically stabilized, covalently attached polyaniline to the molecules/polymer. The materials might be electrically conductive, have new optical properties, etc.

Also, the silanol-modified aniline compounds (ID, IID) can be used to chemically graft (covalent attachment) the aniline (or protected aniline) function onto silanol or alkoxy silane-containing molecules or polymers to give aniline-attached functions to these molecules/polymers. This may be used for the covalent attachment (chemical stabilization) to sol gels. Subsequent oxidative aniline polymerization will give chemically stabilized, covalently attached polyaniline to the molecules/polymer-sol gel matrix aerogels/xerogels, etc. The materials might be electrically conductive, have new optical properties, etc.

Finally, alpha,omega substituted aniline molecules (Formula 2) might be used for organic modified silicate ("ORMOSIL") stabilization of the sol gel/xerogel matrix. Subsequent oxidative aniline polymerization will give chemically stabilized (but not covalently attached) polyaniline to the molecules/polymer-sol gel matrix aerogels/xerogels. The materials might be electrically conductive, have new optical properties, etc.

2. Aromatic Silicone-Containing Polyimides

Oligomers and polymers of Formula 2 may be copolymerized with a dianhydride compound having Formula 3

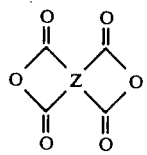

Formula 3 where Z represents

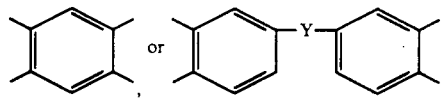

where Y is a direct bond or is a divalent radical selected from the group consisting of —CH$_2$—, —C(CH$_3$)$_2$—, —C(CF$_3$)$_2$—, —O—, —S—, —CO—, —SO$_2$—, and —Si(CH$_3$)$_2$— to give copolymers of Formula 4:

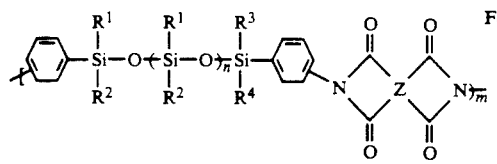

Formula 4

The value of m must be large enough to provide a useful product for material applications. Preferably, m ranges from about 20 to 200, providing soluble, melt-processable, thermally stable polyimides.

The present invention also contemplates alpha,omegaaniline terminated polydimethyl siloxanes (Formula 2) of various molecular weights. The aromatic linkage imparts improved thermal stability to the polymers, as compared to amino aliphatic linkages in current use. The silicone connecting group, which can be of any molecular weight, can impart tailorable properties to the synthesized polyimides. Tailorable properties would be the glass transition point of the polyimides thus formed and the melting point, thus giving melt processable polyimides. In addition, the solubility and toughness of the polymers would be improved.

3. Aromatic Amine-Based Curing Agents.

The alpha,omega-aniline terminated polydimethyl siloxanes (IE, IIE, Formula 2) described in the present invention can be used to cure epoxy or isocyanate resins to give new cured epoxy resins and new polyurethanes. For the same reasons as discussed immediately above, the silicone connector of tailorable molecular weight can be used to adjust the toughness and thermomechanical properties of the resulting materials. In addition, the alpha,omega-aniline terminated polydimethyl siloxanes described herein have unusual reactivity, as compared to the state of the current art. The new curing agents thus represent an opportunity to modify the cure of epoxy or urethane resins. This will increase the shelf life of the formulated resins (for instance, "pre-pregs" and formulated adhesives), and also increase the "out time", tackiness, flow, and pot life of the pre-pregs and adhesives thus formed.

EXAMPLES

General Explanation of Examples

All reactions were carried out under a dry nitrogen atmosphere, using conventional synthetic methodology. The air sensitive reactions were performed using apparatus described by Shriver and Dreizden in the book entitled "Manipulation of Air Sensitive Compounds", Wiley & Sons, 1986.

Gel permeation chromatograms were taken using a Waters chromatography system with Styragel columns standardized with polystyrene standards.

Proton nuclear magnetic resonance (NMR) spectra were recorded at 200 MHz on a Brucker AC200 spectrometer. The residual protons in the CDCl$_3$ solvent were used as a reference at 7.24 parts per million (ppm) because of the complication of adding an extra silicon peak of tetramethylsilane in the NMR spectra. The carbon-13 NMR spectra were recorded at 50.323 MHz on the same instrument. The carbon-13 spectra were referenced to the carbon peak of the solvent CDCl$_3$. The silicon-29 NMR spectra were recorded at 39.765 MHz on the same instrument. The silicon-29 spectra were referenced to tetramethyl silane as an external standard.

Infrared (IR) spectra of liquids and polymers were taken of thin films on NaCl plates. All IR spectra were recorded on a Nicolet MX-1 Fourier transform spectrometer.

The following Examples 1a-c are directed to the preparation of bis (3-aminophenyl)-1,1,3,3-tetramethyl-disiloxane, that is, the 3- (or meta) substituted monomer. Examples 2 and 3 are directed to the preparation of the 3-substituted oligomers and polymers of phenylaminosiloxanes. Compound or formula numbers indicated refer to those previously described herein.

Example 1a

3-Aminophenyldimethyl Silane

This material (IC), which has the formula C$_8$H$_{13}$SiN and molecular weight of 151, is useful as an intermediate and for the incorporation of aromatic amine functionality and polyaniline polymers into vinyl containing polymers via hydrosilation reactions.

1-(3-(dimethylsilyl)phenyl)-2,2,5,5-tetramethyl-1-aza-2,5-disilacyclopentane (31.0 g, 0.105 mol, described in U.S. Pat. No. 5,021,585, assigned to the same assignee as the present application) (IB) was dissolved in tetrahydrofuran (100 mL). To this was added water (2.0 g, 0.11 mol) and a trace of toluene sulfonic acid. The reaction warmed slightly upon addition of the water. After two hours, the contents of the reaction were dried over sodium sulfate, concentrated, and distilled to give a clear mobile liquid (boiling point, or b.p., 110° C./10 torr, or mm of mercury, 14.3 g, 90% yield). The liquid had the following spectral characteristics:

$^1$H NMR (CDCl$_3$):7.23 (m, 1H), 7.02 (m, 1H), 6.90 (m, 1H), 6.75 (m, 1H), 4.46 (septet, 1H, J=3.7 Hz), 3.40 (brd s, 2H), 0.37 (d, 6H, J=3.7 Hz) ppm.

$^{13}$C NMR (CDCl$_3$):145.6, 138.2, 128.7, 123.9, 120.3, 115.9, −3.4 ppm.

$^{29}$Si NMR (CDCl$_3$):−16.92 ppm.

Example 1b

3-Aminophenyldimethyl Silanol

This material (ID), which has the formula C$_8$H$_{14}$SiON and molecular weight of 167, is useful as an intermediate and for the incorporation of aromatic amine functionality and polyaniline polymers into ceramics via sol-gel type processing.

The aminosilane (15.1 g, 0.10 mol) from Example 1a was dissolved in tetrahydrofuran (50 mL). To this was added an aqueous phosphate buffer solution (5 mL) having a pH of 7 and then 5% Pd on carbon (0.100 g). Evolution of hydrogen was immediate but well-controlled. After two hours, the reaction was filtered through CELITE filter agent (CELITE is a trademark of Johns Manville Corporation), carefully concentrated to about 20 mL, taken up in ether, and dried over sodium sulfate. Careful concentration of this solution afforded a clear mobile liquid (16.0 g, 95% yield). The liquid had the following spectral characteristics:

$^1$H NMR (CDCl$_3$):7.17 (m, 1H), 7.02 (m, 1H), 6.92 (m, 1H), 6.70 (m, 1H), 3.6 (brd m, 3H, amine and silanol), 0.34 (s, 6H) ppm.

$^{13}$C NMR (CDCl$_3$):145.1, 140.5, 128.7, 123.5, 120.0, 116.6, −0.2 ppm.

Example 1c

Bis (3-aminophenyl)-1,1,3,3-Tetramethyldisiloxane

This compound (IE) has the formula C$_{16}$H$_{24}$N$_2$Si$_2$O and molecular weight of 316.

The aminosilanol (5.0 g, 0.030 mol) from Example 1b was dissolved in dry benzene (40 mL) and a trace p-toluene sulfonic acid was added. The reaction was refluxed for four hours. Gas chromatograph analysis of the reaction showed the condensation to be complete. The solution was washed well with water, dried over sodium sulfate, concentrated, and distilled at reduced pressure to give a pale yellow liquid (b.p. 165° C./0.01 torr, 4.0 g, 84% yield). The liquid had the following spectral characteristics:

$^1$H NMR (CDCl$_3$):7.21 (m, 2H), 7.02 (m, 2H), 6.90 (m, 2H), 6.73 (m, 2H), 3.84 (s, 4H), 0.37 (s, 12H) ppm.

$^{13}$C NMR (CDCl$_3$):145.1, 140.9, 128.6, 123.4, 119.9, 116.2, 0.7 ppm.

$^{29}$Si NMR (CDCl$_3$):−1.06 ppm.

IR (thin film):3441, 3356, 3217, 3048, 2955, 2897, 1616, 1589, 1485, 1427, 1292, 1256, 1061, 899 cm$^{-1}$.

Example 2

Equilibration of Octamethyl Tetracyclosiloxane and Bis-1,3-(3-aminophenyl) Tetramethyldisiloxane The equilibration product (Formula 2) has a molecular weight (numerical average) of 850, as determined by 1H NMR.

Into a round bottomed flask (50 mL) was placed one drop of a methanol solution of tetramethyl ammonium hydroxide (20% base). The methanol was evaporated and then octamethyl tetracyclosiloxane (2.5 g, 0.008 mol) and bis-1,3-(3-aminophenyl) tetramethyldisiloxane (1.0 g, 0.0032 mol) from Example 1c were added to the flask. The reaction was stirred magnetically and heated for 18 hours at 100° C. A small aliquot was analyzed by gas chromatography and the reaction judged complete. The flask contained at this point about 15% by weight octamethyl tetracyclosiloxane and 85% by weight mixed oligomers of octamethyl tetracyclosiloxane and the endcapping aminophenylsiloxane. The reaction was cooled, taken up in hexane, and washed three times with saturated ammonium chloride to remove the base. The solution was dried over sodium sulfate, then evaporated on a rotary evaporator to give a yellow mobile liquid (3.1 g, 89% yield). The liquid had the following spectral characteristics:

$^1$H NMR (CDCl$_3$):7.21 (m, 2H), 7.02 (m, 2H), 6.90 (m, 2H), 6.73 (m, 2H), 3.64 (s, 4H), 0.35 (m, 12H), 0.11 (m, 52H) ppm.

$^{13}$C NMR (CDCl$_3$):145.6, 140.8, 128.6, 123.2, 119.5, 116.0, (s, all 2C), 1.1 (m, 16C), 0.7 (s, 4C) ppm. $^{29}$Si NMR (CDCl$_3$):−2.43 (s, 2Si), −20.66 (s, 2Si), −21.78 (s, 6.5Si) ppm.

Discernable in the $^{29}$Si spectra was about 12% by weight of bis-1,3-(3-aminophenyl) tetramethyldisiloxane as seen by the singlet at −1.10.

IR (thin film):3468, 3383, 2963, 1620, 1261, 1092, 1026, 802 cm$^{-1}$.

Example 3

Synthesis of Polyimides Using the Extended Siloxane Diamine From Example 2.

Into a round bottomed flask was placed an extended diamine compound (5.00 g, 0.00347 mol) from Example 2, 6F dianhydride (Formula 3) (1.56 g, 0.00347 mol), and dimethylacetamide solvent (20 mL). The reaction was stirred for 48 hours. At this time, toluene was added (20 mL) and the reaction was refluxed for twelve hours. The toluene was then removed by distillation. The polymer (Formula 4) was isolated by precipitation into water, filtration, drying, redissolving in tetrahydrofuran (THF), and precipitation into water. Drying of the material afforded a light brown solid which was analyzed by proton and carbon NMR. These spectra were consistent with the assigned structure. Inherent viscosity (0.5% in THF) 0.21; IR (neat) 2963, 1782, 1261, 1095, 1022, 802 cm$^{-1}$. Thermal analysis (differential scanning calorimetry) showed a glass transition at about 40° C. and a melt endotherm at about 120° C.

The following Examples 4a–c are directed to the preparation of bis (4-aminophenyl)-1,1,3,3-tetramethyldisiloxane, that is, the 4- (or para) substituted monomer. These 4-substituted compounds are interesting because of their different reactivity as compared to the 3-substituted compounds described above. All of the following compounds are much more easily attacked by acid to give the desilated products. Because of this, all of the reactions were carried out with base catalysis.

Example 4a

4-Aminophenyldimethyl Silane

This compound, which has the formula C$_8$H$_{13}$SiN and molecular weight of 151, is useful as an intermediate and for the incorporation of aromatic amine functionality and polyaniline polymers into vinyl containing polymers via hydrosilation reactions.

1-(4-(Dimethylsilyl)phenyl)-2,2,5,5-tetramethyl-1-aza-2,5-disilacyclopentane (8.8 g, 0.03 mol, described in U.S. Pat. No. 5,021,585) was dissolved in tetrahydrofuran (50 mL). To this was added water (2.0 g, 0.11 mol) and a trace of potassium carbonate. The reaction warmed slightly upon the addition of water. After two hours, the contents of the reaction were dried over sodium sulfate and concentrated to give a clear mobile liquid (4.0 g, 88% yield). The liquid had the following spectral characteristics:

$^1$H NMR (CDCl$_3$):7.34 (m, 2H), 6.69 (m, 2H), 4.40 (septet, 1H, J=3.7 Hz), 3.60 (brd s, 2H), 0.31 (d, 6H, J=3.7 Hz) ppm.

$^{13}$C NMR (CDCl$_3$):147.4, 135.2, 125.1, 114.6, −3.5 ppm.

Example 4b

4-Aminophenyldimethyl Silanol.

This material, which has the formula C$_8$H$_{14}$SiON and molecular weight of 167, is useful as an intermediate and for the incorporation of aromatic amine functionality and polyaniline polymers into ceramics via sol-gel type processing.

The aminosilane (4.8 g, 0.032 mol from Example 4a was dissolved in tetrahydrofuran (50 mL). To this was added an aqueous phosphate buffer solution (2 mL) having a pH of 7 and then 5% Pd on carbon (0.050 g). Evolution of hydrogen was much faster for this para-substituted isomer than for the corresponding meta-substituted isomer. Larger scale reactions of this molecule were conducted at 0° C. and with a minimum of catalyst. After two hours, the reaction was filtered through CELITE filter agent, carefully concentrated to about 20 mL, taken up in ether, and dried over sodium sulfate. Careful concentration of this solution afforded a clear mobile liquid (4.7 g, 89% yield). The liquid had the following spectral characteristics:

$^1$H NMR (CDCl$_3$):7.37 (m, 2H), 6.66 (m, 2H), 3.1 (brd m, 3H, amine and silanol), 0.33 (s, 6H) ppm.

$^{13}$C NMR (CDCl$_3$):147.6, 134.5, 115.2, 114.5, 0.01 ppm.

Example 4c

Bis (4-aminophenyl)-1,1,3,3-Tetramethyldisiloxane

This compound has the formula C$_{16}$H$_{24}$N$_2$Si$_2$O and molecular weight of 316.

The aminosilanol (10.0 g, 0.060 mol) from Example 4b was dissolved in dry benzene (80 mL) and a trace of potassium hydroxide was added. The reaction was refluxed for fourteen hours. Gas chromatograph analysis of the reaction showed the condensation to be complete. The solution was washed well with water, dried over activated molecular sieves, concentrated, and distilled at reduced pressure to give a pale yellow liquid (b.p. 185° C./0.05 torr, 5.2 g, 56% yield). The liquid had the following spectral characteristics:

$^1$H NMR (C$_6$D$_6$):7.45 (m, 4H), 6.41 (m, 4H), 3.04 (brd s, 4H), 0.38 (s, 12H) ppm.

$^{13}$C NMR (CDCl$_3$):147.0, 134.2, 128.1, 114.2, 0.8 ppm.

IR (thin film):3460, 3375, 3016, 2955, 1602, 1597, 1504, 1269, 1253, 1115, 1045, 837, 790 cm$^{-1}$.

Thus, there has been disclosed (a) a process for preparing amine terminated silicone monomers, oligomers, and polymers thereof and (b) certain novel compounds formed thereby. It will be readily apparent to those skilled in this art that various changes and modifications of an obvious nature may be made without departing from the intention of the invention, and all such changes and modifications &re considered to fall within the scope of the invention, as defined by the appended claims.

What is claimed is:

1. A process for forming a compound having Formula 1

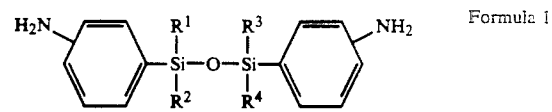

Formula 1 wherein R$^1$, R$^2$, R$^3$, and R$^4$ are independently C$_1$ to C$_6$ alkyl, phenyl, or phenyl substituted with one or more alkyl or halogen groups, comprising the steps of:

(a) reacting a bromoaniline compound with a chosen silating agent to form a compound having the formula

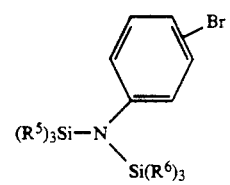

where R$^5$ and R$^6$ are each a C$_1$ to C$_4$ alkyl group or where the group -NSi (R$^5$)$_3$Si(R$^6$)$_3$ is 2,2,5,5-tetramethyl-1-aza-2,5-disilacyclopentane;

(b) reacting the compound formed in Step "a" with an alkyllithium compound or magnesium, followed by reaction with a chosen halogenated silane compound to form a compound having the formula

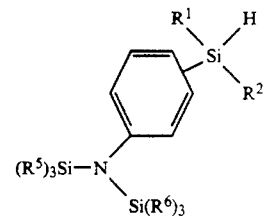

(c) hydrolyzing the compound formed in Step "b" in the presence of acid or base to form a compound having the formula

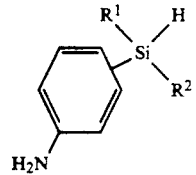

(d) hydrolyzing the compound formed in Step "c" to form a compound having the formula

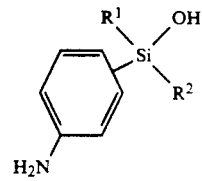

and (e) condensing the compound formed in Step "d" to form the compound having Formula 1.

2. The process of claim 1 wherein said bromoaniline compound is selected from the group consisting of 3-bromoaniline and 4-bromoaniline.

3. The process of claim 1 wherein $R^1$, $R^2$, $R^3$, and $R^4$ are each methyl.

4. The process of claim 1 wherein said compound of Formula 1 is bis(3-aminophenyl)-1,1,3,3-tetramethyl disiloxane.

5. The process of claim 1 wherein said compound of Formula 1 is bis(4-aminophenyl)-1,1,3,3-tetramethyl disiloxane.

6. A process for forming a silane compound having the formula

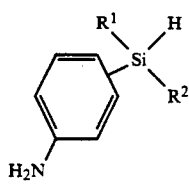

wherein $R^1$ and $R^2$ are independently $C_1$ to $C_6$ alkyl, phenyl, or phenyl substituted with one or more alkyl or halogen groups, comprising the steps of:

(a) reacting a bromoaniline compound with a chosen silating agent to form a compound having the formula

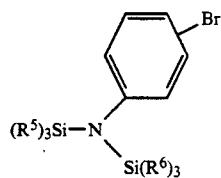

where $R^5$ and $R^6$ are each a $C_1$ to $C_4$ alkyl group or where the group $-NSi(R^5)_3Si(R^6)_3$ is 2,2,5,5-tetramethyl-1-aza-2,5-disilacyclopentane;

(b) reacting the compound formed in Step "a" with an alkyllithium compound or magnesium, followed by reaction with a chosen halogenated silane compound to form a compound having the formula

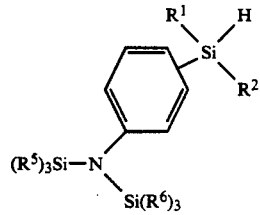

and (c) hydrolyzing the compound formed in Step "b" in the presence of acid or base to form said silane compound.

7. The process of claim 6 wherein said bromoaniline compound is selected from the group consisting of 3-bromoaniline and 4-bromoaniline.

8. The process of claim 6 wherein $R^1$ and $R^2$ are each methyl.

9. A process for forming a silanol compound having the formula

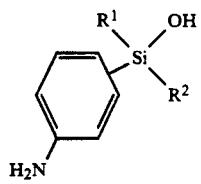

wherein $R^1$ and $R^2$ are independently $C_1$ to $C_6$ alkyl, phenyl, or phenyl substituted with one or more alkyl or halogen groups, comprising the steps of:

(a) reacting a bromoaniline compound with a chosen silating agent to form a compound having the formula

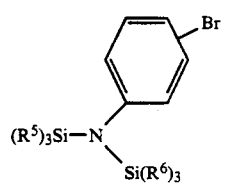

where $R^5$ and $R^6$ are each a $C_1$ to $C_4$ alkyl group or where the group $-NSi(R^5)_3Si(R^6)_3$ is 2,2,5,5-tetramethyl-1-aza-2,5-disilacyclopentane;

(b) reacting the compound formed in Step "a" with an alkyllithium compound or magnesium, followed by reaction with a chosen halogenated silane compound to form a compound having the formula

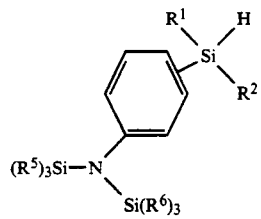

(c) hydrolyzing the compound formed in Step "b" in the presence of acid or base to form a compound having the formula

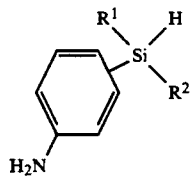

(d) hydrolyzing the compound formed in Step "c" to form said silanol compound.

10. The process of claim 9 wherein said bromoaniline compound is selected from the group consisting of 3-bromoaniline and 4-bromoaniline.

11. The process of claim 9 wherein $R^1$ and $R^2$ are each methyl.

12. A process for forming an oligomer having Formula 2

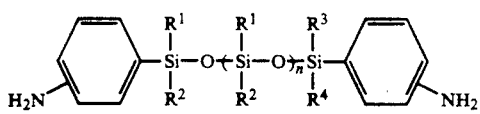
Formula 2 wherein $R^1$, $R^2$, $R^3$, and $R^4$ are independently $C_1$ to $C_6$ alkyl, phenyl, or phenyl substituted with one or more alkyl or halogen groups and wherein n is 1 to 20, comprising the steps of:

(a) reacting a bromoaniline compound with a chosen silating agent to form a compound having the formula

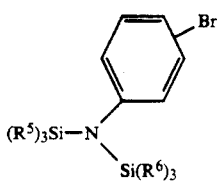

where $R^5$ and $R^6$ are each a $C_1$ to $C_4$ alkyl group or where the group $-NSi(R^5)_3Si(R^6)_3$ is 2,2,5,5-tetramethyl-1aza-2,5-disilacyclopentane;

(b) reacting the compound formed in Step "a" with an alkyllithium compound or magnesium, followed by reaction with a chosen halogenated silane compound to form a compound having the formula

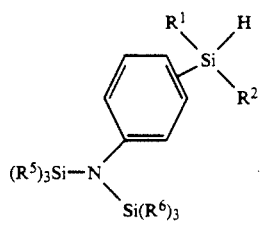

(c) hydrolyzing the compound formed in Step "b" in the presence of acid or base to form a compound having the formula

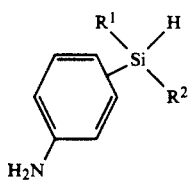

(d) hydrolyzing the compound formed in Step "c" to form a compound having the formula

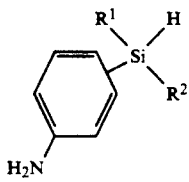

(e) condensing the compound formed in Step "d" to form a compound having Formula 1

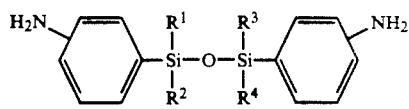
Formula 1 and (f) reacting said compound of Formula 1 with a cyclic siloxane having $\geq 3$ silicon atoms, each substituted with $R^1$ and $R^2$ as defined above to form said compound having Formula 2.

13. The process of claim 12 wherein said cyclic siloxane comprises octamethyl tetracyclosiloxane.

14. The process of claim 12 wherein said bromoaniline compound is selected from the group consisting of 3-bromoaniline and 4-bromoaniline.

15. The process of claim 12 wherein $R^1$, $R^2$, $R^3$, and $R^4$ are each methyl.

16. The process of claim 12 wherein said compound of Formula 1 is selected from the group consisting of bis(3-aminophenyl)-1,1,3,3-tetramethyl disiloxane and bis(4-aminophenyl)-1,1,3,3-tetramethyl disiloxane.

17. A process for forming a polymer having Formula 4

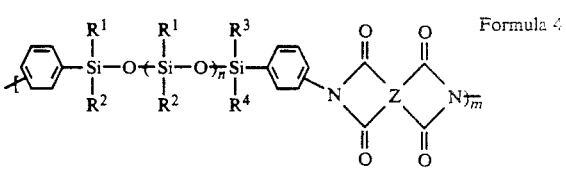
Formula 4 wherein $R^1$, $R^2$, $R^3$, and $R^4$ are independently $C_1$ to $C_6$ alkyl, phenyl, or phenyl substituted with one or more alkyl or halogen groups, wherein n is 1 to 20, wherein m is about 20 to 200, and wherein Z represents

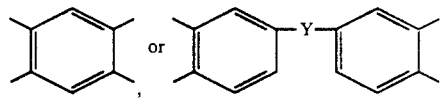

where Y is a divalent bond or a divalent radical selected from the group consisting of $-CH_2-$, $-C(CH_3)_2-$, $-C(CF_3)_2-$, $-O-$, $-S-$, $-CO-$, $-SO_2-$, and $-Si(CH_3)_2-$, comprising the steps of:

(a) reacting a bromoaniline compound with a chosen silating agent to form a compound having the formula

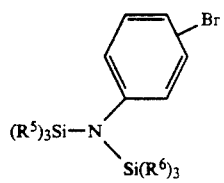

where $R^5$ and $R^6$ are each a $C_1$ to $C_4$ alkyl group or where the group $-NSi(R^5)_3Si(R^6)_3$ is 2,2,5,5-tetramethyl-1-aza-2,5-disilacyclopentane;

(b) reacting the compound formed in Step "a" with an alkyllithium compound or magnesium, followed by reaction with a chosen halogenated silane compound to form a compound having the formula

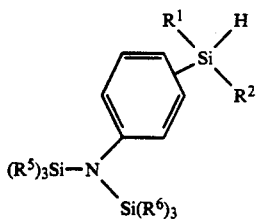

(c) hydrolyzing the compound formed in Step "b" in the presence of acid or base to form a compound having the formula

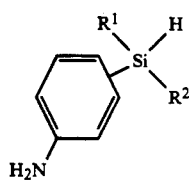

(d) hydrolyzing the compound formed in Step "c" to form a compound having the formula

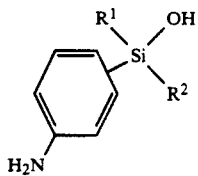

(e) condensing the compound formed in Step "d" to form a compound having Formula 1

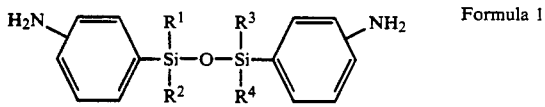

Formula 1

(f) reacting said compound of Formula 1 with a cyclic siloxane having ≧3 silicon atoms, each substituted with $R^1$ and $R^2$ as defined above to form a compound having Formula 2:

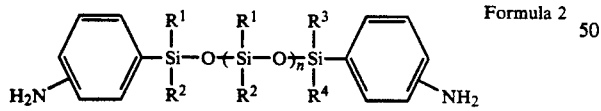

Formula 2 and (g) reacting said compound of Formula 2 with an anhydride having Formula 3

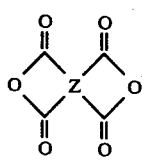

Formula 3 to form said copolymer having Formula 4.

18. The process of claim 17 wherein said cyclic siloxane comprises octamethyl tetracyclosiloxane.

19. The process of claim 17 wherein said bromoaniline compound is selected from the group consisting of 3-bromoaniline and 4-bromoaniline.

20. The process of claim 17 wherein $R^1$, $R^2$, $R^3$, and $R^4$ are each methyl.

21. The process of claim 17 wherein said compound of Formula 1 is selected from the group consisting of bis(3-aminophenyl)-1,1,3,3-tetramethyl disiloxane and bis(4-aminophenyl)-1,1,3,3-tetramethyl disiloxane.

22. The process of claim 17 wherein Y is —C(CF$_3$)$_2$—.

23. A compound having Formula 5

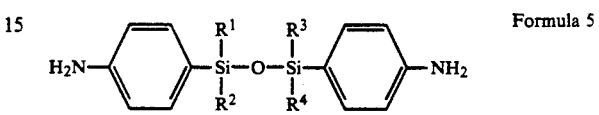

Formula 5 where $R^1$, $R^2$, $R^3$, and $R^4$ are independently $C_1$ to $C_6$ alkyl, phenyl, or phenyl substituted with one or more alkyl or halogen groups.

24. The compound of claim 23 wherein $R^1$, $R^2$, $R^3$, and $R^4$ are each methyl.

25. A compound having the formula

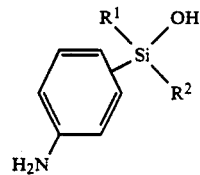

where the silyl group is in the meta or para position and where $R^1$ and $R^2$ are independently $C_1$ to $C_6$ alkyl, phenyl, or phenyl substituted with one or more alkyl or halogen groups.

26. The compound of claim 25 wherein $R^1$ and $R^2$ are each methyl.

27. A compound having the formula

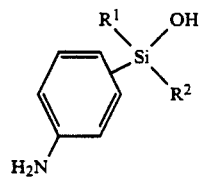

where the silanol group is in the meta or para position and where $R^1$ and $R^2$ are independently $C_1$ to $C_6$ alkyl, phenyl, or phenyl substituted with one or more alkyl or halogen groups.

28. The compound of claim 27 wherein $R^1$ and $R^2$ are each methyl.

29. A compound having Formula 2

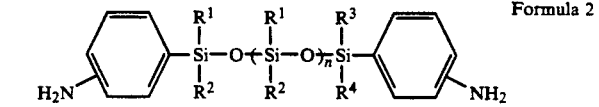

Formula 2 wherein $R^1$, $R^2$, $R^3$, and $R^4$ are independently $C_1$ to $C_6$ alkyl, phenyl, or phenyl substituted with one or more alkyl or halogen groups and wherein n is 1 to 20.

30. The compound of claim 29 wherein $R^1$, $R^2$, $R^3$, and $R^4$ are each methyl.

31. A polymer having Formula 4

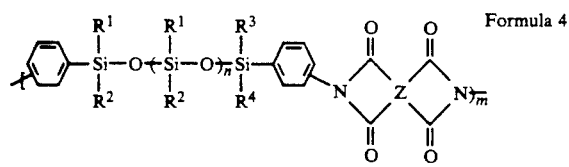

Formula 4 wherein $R^1$, $R^2$, $R^3$, and $R^4$ are independently $C_1$ to $C_6$ alkyl, phenyl, or phenyl substituted with one or more alkyl or halogen groups, wherein n is 1 to 20, wherein m is about 20 to 200, and wherein Z represents

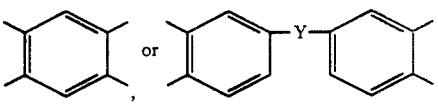

where Y is a divalent bond or a divalent radical selected from the group consisting of $-CH_2-$, $-C(CH_3)_2-$, $-C(CF_3)_2-$, $-O-$, $-S-$, $-CO-$, $-SO_2-$, and $-Si(CH_3)_2-$.

32. The compound of claim 29 wherein $R^1$, $R^2$, $R^3$, and $R^4$ are each methyl.

* * * * *